(12) United States Patent
Ruschel et al.

(10) Patent No.: US 8,865,936 B2
(45) Date of Patent: Oct. 21, 2014

(54) VEGETAL OIL DERIVATIVES

(75) Inventors: Roberto Chaves Barcellos Ruschel, Porto Alegre (BR); Gilberto Martins Junior, Sao Sebastiao do Cai (BR)

(73) Assignee: SGS Polimeros Ltda, São Sebastiao do Cai (BR)

( * ) Notice: Subject to any disclaimer, the term of this patent is extended or adjusted under 35 U.S.C. 154(b) by 159 days.

(21) Appl. No.: 12/446,691

(22) PCT Filed: Aug. 29, 2008

(86) PCT No.: PCT/BR2008/000260
§ 371 (c)(1),
(2), (4) Date: Apr. 22, 2009

(87) PCT Pub. No.: WO2009/033240
PCT Pub. Date: Mar. 19, 2009

(65) Prior Publication Data
US 2010/0010126 A1    Jan. 14, 2010

(30) Foreign Application Priority Data

Sep. 12, 2007 (BR) ..................................... 0704776

(51) Int. Cl.
| | | |
|---|---|---|
| *C07C 53/08* | (2006.01) | |
| *C08K 5/1515* | (2006.01) | |
| *C08K 5/10* | (2006.01) | |
| *C11C 3/10* | (2006.01) | |
| *C07C 67/02* | (2006.01) | |
| *C08K 5/103* | (2006.01) | |

(52) U.S. Cl.
CPC ................. *C08K 5/10* (2013.01); *C08K 5/1515* (2013.01); *C11C 3/10* (2013.01); *C07C 67/02* (2013.01); *C08K 5/103* (2013.01)
USPC .......................................................... 562/607

(58) Field of Classification Search
CPC .................................. C07C 67/02; C11C 3/10
USPC ........... 524/114, 290, 308, 317, 320; 562/607
See application file for complete search history.

(56) References Cited

U.S. PATENT DOCUMENTS 3,281,382 A * 10/1966 Kuester et al. ................ 524/114
7,071,343 B2 * 7/2006 Daute et al. ................... 549/514

FOREIGN PATENT DOCUMENTS

CN         101113354 A  *  1/2008

OTHER PUBLICATIONS

Food Standards Agency, "Fats and Oils", McCance & Widdowson's the Composition of Foods, Royal Society of Chemistry, 1991.*
"Biodiesel Fuel Production by Transesterification of Oils" by Fukuda et al. J of Bioscience and Bioengineering. vol. 92, No. 5, 405-416, 2001.*
Modi et al ("Lipase-mediated conversion of vegetable oils into biodiesel using ethyl acetate as acyl acceptor", Bioresource Technology 98 (2007) 1260-1264).*
Machine translation of CN 101113354 A, 2008.*
Biodisel production from rapeseed oil by various supercritical carboxylate esters; Goembira, Fadjar et al.; Jul. 2012; http://hdl.handle.net/2433/156289.
Journal of Food Technology 2005; Modification of beef tallow stearin and olein by chemical and enzymatic interesterification with soybean oil ; Kowalska et al.

* cited by examiner

*Primary Examiner* — Ling Choi
*Assistant Examiner* — Wenwen Cai
(74) *Attorney, Agent, or Firm* — Patent Law Agency, LLC; Peter Ganjian

(57) ABSTRACT

This invention comprises the use of the interesterification reaction between vegetal or animal oils and esters from monoacids (preferentially with 1 to 12 carbons) and monoalcohols (preferentially with 1 to 12 carbons). The use of ethyl acetate is preferred as it is a product that may be obtained from ethanol (renewable) and has a boiling point (77° C.), which facilitates separation by vacuum distillation at the end of the reaction and its reuse. By varying the molar ratio between glycerol triester (oil or fat) and monoalcohol ester, different proportions of glycerol esters are obtained with 1 or 2 linked fatty acids and 1 or 2 linked acids of short chain, along with the formation of fatty acid ester of monoalcohol. After the distillation of excess residual ethyl acetate, products are obtained with viscosity from 21 to 33 cPs at 25° C., in the case of the reaction with soy oil.

3 Claims, 1 Drawing Sheet

VEGETAL OIL DERIVATIVES

TECHNICAL FIELD

The following descriptive report of the invention application refers to the development of oil vegetal derivatives comprising the use of the interesterification reaction between vegetal or animal oils and monoacid esters (preferentially with 1 to 12 carbons) and monoalcohol esters (preferentially with 1 to 12 carbons) The use of ethyl acetate is preferred as it is a product that can be obtained from ethanol (renewable) and has a low boiling point (77° C.), which facilitates the separation by vacuum distillation at the end of the reaction and its reuse.

Vegetal oils are interesterified with monoacid and monoalcohol esters, in the presence of a catalyst, generating a mixture of glycerol esters with short and long chain acids simultaneously bound to polyol. Also fatty acid esters are formed with alcohol. The product from this reaction may be epoxidized with hydrogen peroxide, obtaining a low viscosity product applied as a plasticizer for polar polymers such as PVC and NBR.

ART BACKGROUND

Oils with the composition proposed in this patent were not found in the technical literature or described in patents. All one finds are products derived from the triacetin (glycerol triacetate) interesterification reaction with triglycerides.

The process is described in the U.S. Pat. N. 5,434,278, which suggests a combination of triacetin with tripropionin and tributyrin to get around the problem of low solubility of triacetin in oils and fats with resulting reaction difficulty. This problem does not occur in the reaction with monoalcohol and monoacid esters.

It can be predicted that oils with the composition that has been obtained will have applications as emollients in cosmetics, solvents for use in industrial and home cleaning, plasticizers for low-polarity polymers such as natural and synthetic rubbers, and as a fluid for use in petroleum well drilling.

The interesterification reaction was repeated, replacing the vegetal oil with epoxidized vegetal oil. With this, it was intended to obtain a product of greater polarity and greater stability to oxidation, aiming at its application as plasticizer for polymers of greater polarity such as, for example, vinyl polychloride and rubbers containing acrylonitrile.

The most used plasticizers for this purpose are the esters from phthalic anhydride, the phthalates.

The U.S. Pat. No. 6,734,241 proposes the use of monoglycerides from castor bean oil or hydrogenated castor bean acetylated as plasticizers and it demonstrates its efficiency for PVC plasticization. The problem is that the product would have a high production cost due to the production process and the cost of the castor bean oil.

The U.S. Pat. No. 7,071,343 proposes the use of the product from the interesterification of epoxidized vegetal oil with triacetin (glycerol triester with acetic acid) or the interesterification of triacetin with epoxidized fatty acid methyl ester.

The reaction of the epoxidized vegetal oil with triacetin is carried out at 220° C. in the presence of a catalyst for 3-4 hours in the examples.

In a comparative evaluation with DOP and DOA and using up to 100 PHR plasticizer in combination with PVC, no exudation occurred. Shore A hardness was higher than that obtained with DOP. Thermal stability at 180° C. was substantially improved.

The U.S. Pat. No. 5,643,301 assesses the effect of zinc stearate used as thermal stabilizer in PVC composites, containing esters from epoxidized fatty acids, and concludes that the maximum content of zinc stearate must be 0.1% of the PVC mass, otherwise the zinc chloride formed may catalyze the thermal degradation of the polymer and also polymerization reactions of the epoxidized esters may occur, causing defects on the surfaces of the pieces produced.

DESCRIPTION OF THE INVENTION

Figure 1:
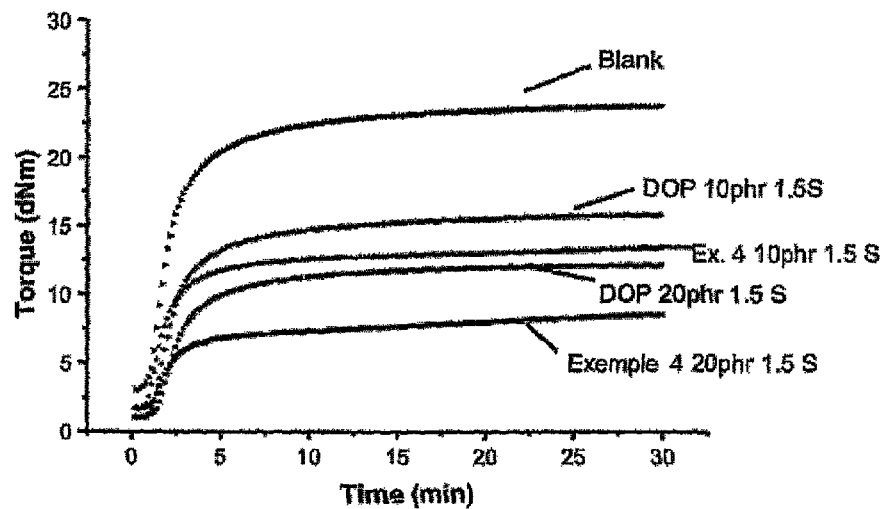
FIG. 1 shows the overlapping of the rheometric curves obtained for the five compounds.
Figure 2:
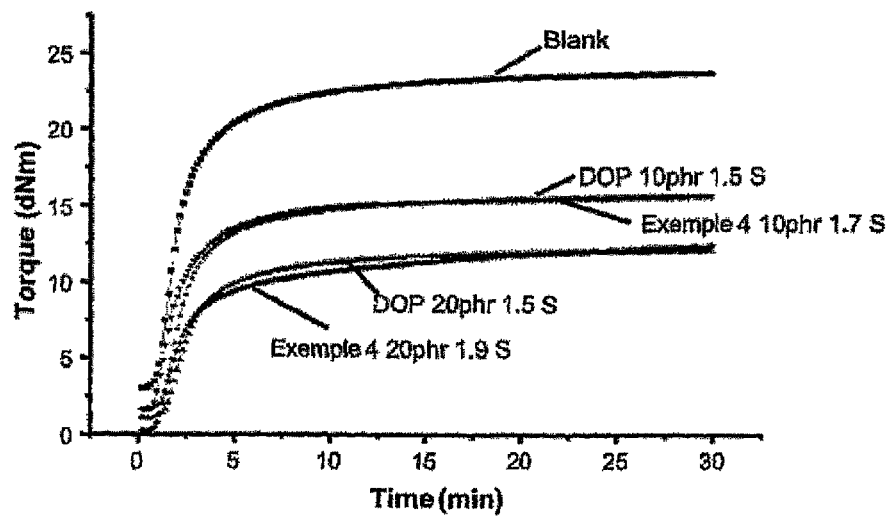
FIG. 2 shows the overlapping of rheometric curves following the adjustment of the sulfur content.

The objective of this invention is to obtain plasticizers derived from renewable feedstock, combining suitable availability of raw material, low energy consumption, low impact of generated effluents, effectiveness in the final performance as plasticizer, biodegradability, and biocompatibility. For this purpose, compounds were synthesized containing glycerol esters with short chain acids (preferentially acetates) and epoxidized fatty acids, in a combination with epoxidized fatty acid esters of monoalcohol (preferentially ethanol).

The interesterification process according to the present invention is catalyzed by basic compounds such as lithium, sodium or potassium hydroxides, and preferentially by alkoxides from these metals such as sodium or potassium methoxide. The necessary amount of catalyst ranges from 0.01% to 1% by weight and more particularly between 0.3% and 0.6% by weight.

The achievement process is carried out at a temperature from 60° C. to 125° C. To facilitate viewing the reaction the following formulas are established:

G(F)3—glycerol triester with 3 fatty acids;
Et-Ac—ethyl acetate;
G(F)2 Ac—ester glycerol with 2 fatty acids and 1 acetic acid;
GF(Ac)2—ester glycerol with 1 mol fatty acid and 2 mol acetic acid;
Et-F—fatty acid ethyl ester.

In the presence of a catalyst and at a suitable temperature, a redistribution of different acids bound to alcohols occurs.

The composition obtained depends on the proportion between reagents.

It has been determined that for obtaining a product with an average composition of 1 mol G(F)2Ac plus 1 mol Et-F an excess of 40% ethyl acetate must be used.

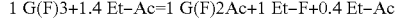

1 G(F)3+1.4 Et–Ac=1 G(F)2Ac+1 Et–F+0.4 Et–Ac

To obtain a product with an average composition of 1 mol G-F(Ac)2 plus 2 mol Et-F, an excess of 100% ethyl acetate must be used.

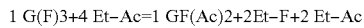

1 G(F)3+4 Et–Ac=1 GF(Ac)2+2Et–F+2 Et–Ac

After reaching the reaction equilibrium, the catalyst is neutralized with acid and the excess volatile ester is vacuum distilled. The salt formed is removed via filtration.

Using vegetal oil such as soy oil, esters are obtained which contain unsaturations derived from oleic, linoleic and linolenic acids.

From the epoxidized vegetal oil a composition is achieved with the same ester composition, but with the difference that unsaturations are replaced with oxirane groups.

There is no hindrance or prejudice if interesterification is performed first and then epoxidation, which is a public domain process, and in industrial scale is usually performed using peracids such as performic or peracetic acids generated in situ by the reaction of organic acids with hydrogen peroxide.

As for the oils used, it is desirable that these do not contain a very high concentration of saturated fatty acids, as these cannot be epoxidized and, consequently, generate products of lower polarity.

EXAMPLES

Substances used:
Epoxidized soy oil—Olvex 60, SGS Polimeros Ltda.
Ethyl acetate—Rhodia (99.5% minimum)
Sodium methoxide—Degussa (29.5% minimum)
Glacial acetic acid—Rhodia (99.5% minimum)
Vinyl polychloride—Norvic SP 1000 (Braskem®)
Dioctyl phthalate—Elekeiroz (99%)
Diisobutylphthalate—Elekeiroz (99%)
NBR (acrylonitrile/butadiene rubber)—N 515B (Nitrflex)
Ca/Zn Markstab IBZ-524 stabilizer (Inbra)
Accelerator—Linkwell TBBS (N-tert butyl-2-benzothiazol sulfenamide)

Example 1

Interesterification of soy oil with ethyl acetate to obtain a product with molar ratio G(F)2 Ac/EtF=1.

Load the reactor equipped with stirring system and condenser with 879 g soy oil, 123 g ethyl acetate, and heat at 90° C. under nitrogen atmosphere. Add 4.4 g sodium methoxide. Heat at 115° C. and maintain for 1 hour. Add 1.5 g acetic acid to neutralize the catalyst. Heat at 125° C, distilling the excess ethyl acetate.

Create vacuum by maintaining for 1 hour a 40 mmHg absolute pressure.

Cool at 90° C. and add 88 g water for washing, keeping under stirring for 1 hour.

Decant for 1 hour and drain the water phase. Reheat at 125° C. and reapply vacuum for drying until the humidity content is below 0.2%.

A 948 g product is generated, and 49 g ethyl acetate is recovered by condensation.

Characterization of the product obtained:

| | |
|---|---|
| Water content by Karl Fisher | 0.028%; |
| Saponification index | 218.300 mg KOH/gram; |
| Acidity index | 44.000 mg KOH/g; |
| Brookfield viscosity at 25° C. | 33.000 cPs (spindle 1/100 rpm); |
| Density at 20° C. | 0.927 g/cm³. |

Example 2

Interesterification of soy oil with ethyl acetate to obtain a product with molar ratio GF(Ac)2/EtF=0.5.

The reactor was loaded with 879 g soy oil and 325 g ethyl acetate.

The process from example 1 was repeated with the same amount of catalyst (4.4 g), and 1050 g of the product was obtained and 175 g ethyl acetate was recovered.

Characterization of the product obtained:

| | |
|---|---|
| Water content by Karl Fisher | 0.027%; |
| Saponification index | 237.00 mg KOH/gram; |
| Acidity index | 1.63 mg KOH/g; |
| Brookfield viscosity at 25° C. | 21.0 cPs (spindle 1/100 rpm); |
| Density at 20° C. | 0.919 g/cm³. |

Example 3

Interesterification of epoxidized soy oil with ethyl acetate to obtain a product with molar ratio G(F)2 Ac/EtF=1.

The reactor was loaded with 940 g epoxidized soy oil with 6.5% oxirane content and 123 g ethyl acetate.

The conditions of the example 1 were repeated, but the amount of sodium methoxide was increased to 46 g. 1010 g of the product was generated, and 46 g ethyl acetate was recovered by condensation.

| | |
|---|---|
| Water content by Karl Fisher | 0.082%; |
| Acidity index | 0.95 mg KOH/g; |
| Brookfield viscosity at 25° C. | 150.0 cPs (spindle 1/20 rpm); |
| Density at 20° C. | 0.988 g/cm³; |
| Epoxy content | 5.85%; |
| Iodine index | 1.15 gI2/100 g sample |

Example 4

Interesterification of epoxidized soy oil with ethyl acetate to obtain a product with molar ratio G(F)2 Ac/EtF=0.5.

The reactor was loaded with 940 g epoxidized soy oil with 6.5% oxirane content and 325 g ethyl acetate.

The conditions from example 1 were repeated, but the amount of sodium methoxide was increased to 46 g.

1095 g of the product was generated, and 48 g ethyl acetate was recovered by condensation.

| | |
|---|---|
| Water content by Karl Fisher | 0.105%; |
| Acidity index | 0.830 mg KOH/g; |
| Brookfield viscosity at 25° C. | 78.0 cPs (spindle 1/50 rpm); |
| Density at 20° C. | 0.994 g/cm³; |
| Epoxy content | 5.06%; |
| Iodine index | 1.19 gI2/100 g sample |

Application Examples

The performance of the product obtained was compared with DOP in nitrile rubbers compounds and also in combination with PVC.

The physical-mechanic properties of nitrile rubber compounds (Nitriflex N 615B) were assessed, these contained 33% acrylonitrile and were plasticized with dioctylphthalate and with the product obtained in example 4. The formulation is based on the ASTM D3187-00 standard.

Rheometric curves were performed at 170° C. The sulfur content of the compounds was adjusted to achieve similar rheologic curves. The results can be seen in Tables 1 and 2.

Table 3 shows the physical-mechanical and chemical properties for the white compound, 10 phr DOP, 20 per DOP, for example 4-10 phr, and for example 4-20 phr.

Table 4 shows the rheometric curve for 10 phr DOP, 20 phr DOP, for example 4-10 phr, and for example 4-20 phr.

Table 5 shows accelerated aging at an oven, 70 h at 125° C. for 10 phr DOP, 20 phr DOP, for example 4-10 phr, and for example 4-20 phr.

Table 6 shows the permanent deformation under compression test at 22 h and 124° C. for 10 phr DOP, 20 phr DOP, for example 4-10 phr, and for example 4-20 phr.

The product obtained in example 4 was evaluated as a plasticizer for a PVC resin. The resin Norvic® SP 1000 (Braskem®) was used, which is a homopolymer obtained in suspension, with k value (DIN 53726) of 65+1 and 95% of particles larger than 63 microns. The amount of plasticizers was determined to obtain a Shore A hardness of 65, using as plasticizers DOP (dioctylphthalate), IDBP (diisobutylphthalate), and the plasticizer obtained in example 4. As a thermal stabilizer, the product Markstab® IBZ-524 was used at 2.4% by weight on the resin along with 5% epoxidized soy oil (Olvex 60). For each 100 parts by PVC weight it was necessary to use the following amounts of plasticizers.

| | |
|---|---|
| DOP | 78.0 phr; |
| DIBP | 68.4 phr; |
| Example 4 | 73.9 phr. |

The product obtained in example 4 presented an intermediate plasticization ability between DOP and IDBP. The test pieces were examined after 6 months and did not show any migration sign.

TABLE 01

| Ingredients | White Compound | DOP 10 phr | DOP 20 phr | Example 4 10 phr | Example 4 20 phr |
|---|---|---|---|---|---|
| NBR rubber | 100.0 | 100.0 | 100.0 | 100.0 | 100.0 |
| Zinc oxide | 3.0 | 3.0 | 3.0 | 3.0 | 3.0 |
| Stearic acid | 1.0 | 1.0 | 1.0 | 1.0 | 1.0 |
| Carbon Black | 60.0 | 60.0 | 60.0 | 60.0 | 60.0 |
| DOP | | 10.0 | 20.0 | | |
| OLVEX 50 | | | | 10.0 | 20.0 |
| Accelerator | 0.7 | 0.7 | 0.7 | 0.7 | 0.7 |
| Sulfur | 1.5 | 1.5 | 1.5 | 1.7 | 1.9 |
| Total | 166.2 | 176.2 | 186.2 | 176.4 | 186.6 |

TABLE 02

Physical-mechanical and chemical properties

| | White compound | DOP 10 phr | DOP 20 phr | Example 4 10 phr | Example 4 20 phr |
|---|---|---|---|---|---|
| Shore A hardness | 73 | 65 | 60 | 67 | 61 |
| Tensile breaking strength | | | | | |
| MPa (median) | 22.9 | 20.1 | 19.1 | 20.0 | 18.5 |
| kgf/cm² | 234 | 205 | 195 | 204 | 189 |
| psi | 3320 | 2920 | 2770 | 2900 | 2680 |
| Elongation to break % | 430 | 500 | 490 | 500 | 510 |

TABLE 03

| | White compound | DOP 10 phr | DOP 20 phr | Example 4 10 phr | Example 4 20 phr |
|---|---|---|---|---|---|
| Brittle temperature | −34° C. | −33° C. | −35° C. | −33° C. | −34° C. |
| Acetone extract content | 4 | 11 | 15 | 10 | 14 |

TABLE 04

Rheometric curve: arch ± 0.5°, temperature 170° C., time 30 min, frequency 100 cpm

| | DOP 10 phr | DOP 20 phr | Example 4 10 phr | Example 4 20 phr |
|---|---|---|---|---|
| Minimum torque - ML, dN · m | 1.8 | 1.1 | 1.7 | 1.1 |
| Maximum torque - MH, dN · m | 16.2 | 12.2 | 15.9 | 13.6 |
| Pre-vulcanization time - ts1, min | 1.3 | 1.5 | 1.0 | 1.0 |
| Optimal cure time - t90, min | 8.0 | 8.0 | 6.2 | 11.5 |

TABLE 05

Accelerated aging at oven, 70 h at 125° C.

| | DOP 10 phr | DOP 20 phr | Example 4 10 phr | Example 4 20 phr |
|---|---|---|---|---|
| Shore A harness (median) | 82 | 83 | 80 | 77 |
| Tensile strength - MPa (median) | 6.9 | 5.5 | 7.4 | 7.5 |
| Elongation to break, % (median) | 40 | 30 | 50 | 60 |
| Shore A hardness variation, points | +14 | +21 | +14 | +15 |
| Tensile strength variation, % | −66 | −71 | −63 | −59 |
| Elongation to break variation, % | −92 | −94 | −90 | −88 |

TABLE 06

Permanent Deformation at Compression Test, 22 h at 125° C.

| | DOP 10 phr | DOP 20 phr | Example 4 10 phr | Example 4 20 phr |
|---|---|---|---|---|
| Compression deformation | 67 | 70 | 75 | 76 |

The invention claimed is:

1. A process for producing Fatty Glyceride Acetates which comprises, reacting glycerol fatty esters and ethyl acetate;

glycerol fatty esters are epoxidized soybean oil;

the Fatty Glyceride Acetates having an average composition of 1 mol GF (Ac)2 plus 2 mols of Et-F, when using an excess of 100 % in mol of ethyl acetate in accordance with:

$$1G(F)3 + 4Et\text{-}Ac \Rightarrow 1GF(Ac)2 + 2Et\text{-}F + 2Et\text{-}Ac$$

where:

G(F)3 is glycerol triester with 3 fatty acids;

Et-Ac is ethyl acetate;

GF(Ac)2 is glycerol ester with 1 mol of fatty acid and 2 mols of acetic acid; and Et-F is fatty acid ethyl ester.

2. The process of claim 1 wherein the process is carried out in presence of an interesterification catalyst.

3. The process of claim 1 wherein the process is carried out at temperatures of from 60 to 125 degrees Celsius.

* * * * *